(12) United States Patent
Schnell et al.

(10) Patent No.: US 7,892,208 B2  
(45) Date of Patent: Feb. 22, 2011

(54) MEDICAL TUBING SET SHEATH

(75) Inventors: William J. Schnell, Libertyville, IL (US); David Bell, Grayslake, IL (US); David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 685 days.

(21) Appl. No.: 11/495,046

(22) Filed: Jul. 28, 2006

(65) Prior Publication Data

US 2008/0082052 A1   Apr. 3, 2008

(51) Int. Cl.
  *A61M 5/178* (2006.01)
  *A61M 5/32* (2006.01)
(52) U.S. Cl. .................. 604/165.03; 604/165.04; 604/163; 604/162
(58) Field of Classification Search ............ 604/165.03, 604/263, 166.01, 206, 164.07, 164.08
  See application file for complete search history.

(56) References Cited

U.S. PATENT DOCUMENTS

| | | | |
|---|---|---|---|
| 4,327,723 A * | 5/1982 | Frankhouser | 604/171 |
| 4,941,881 A * | 7/1990 | Masters et al. | 604/162 |
| 5,279,597 A * | 1/1994 | Dassa et al. | 604/535 |
| 5,370,624 A * | 12/1994 | Edwards et al. | 604/167.05 |
| 5,385,372 A | 1/1995 | Utterberg | |
| 5,620,427 A * | 4/1997 | Werschmidt et al. | 604/535 |
| 5,772,638 A | 6/1998 | Utterberg et al. | |
| 5,983,947 A | 11/1999 | Utterberg | |

* cited by examiner

Primary Examiner—Kevin C Sirmons  
Assistant Examiner—Michael J Anderson  
(74) Attorney, Agent, or Firm—Seyfarth Shaw LLP

(57) ABSTRACT

A medical tubing set sheath is provided which includes a retention portion for attaching the sheath to a collar of a connector attached to the medical tubing set. The sheath may serve as a handle to facilitate torque-locking of the connector to another connector. The sheath may also include a ratcheting mechanism in order to allow for the sheath to ratchet upon application of excess torque, when the tubing set is being attached to a peripheral tubing set. The sheath may also include a needle receiving portion, so that the sheath provides for a needle protector, which may be retained in a position displaced from the needle in order to insure that the needle is exposed when removed from its packaging, and can be quickly and easily inserted in a patient's arm.

32 Claims, 3 Drawing Sheets

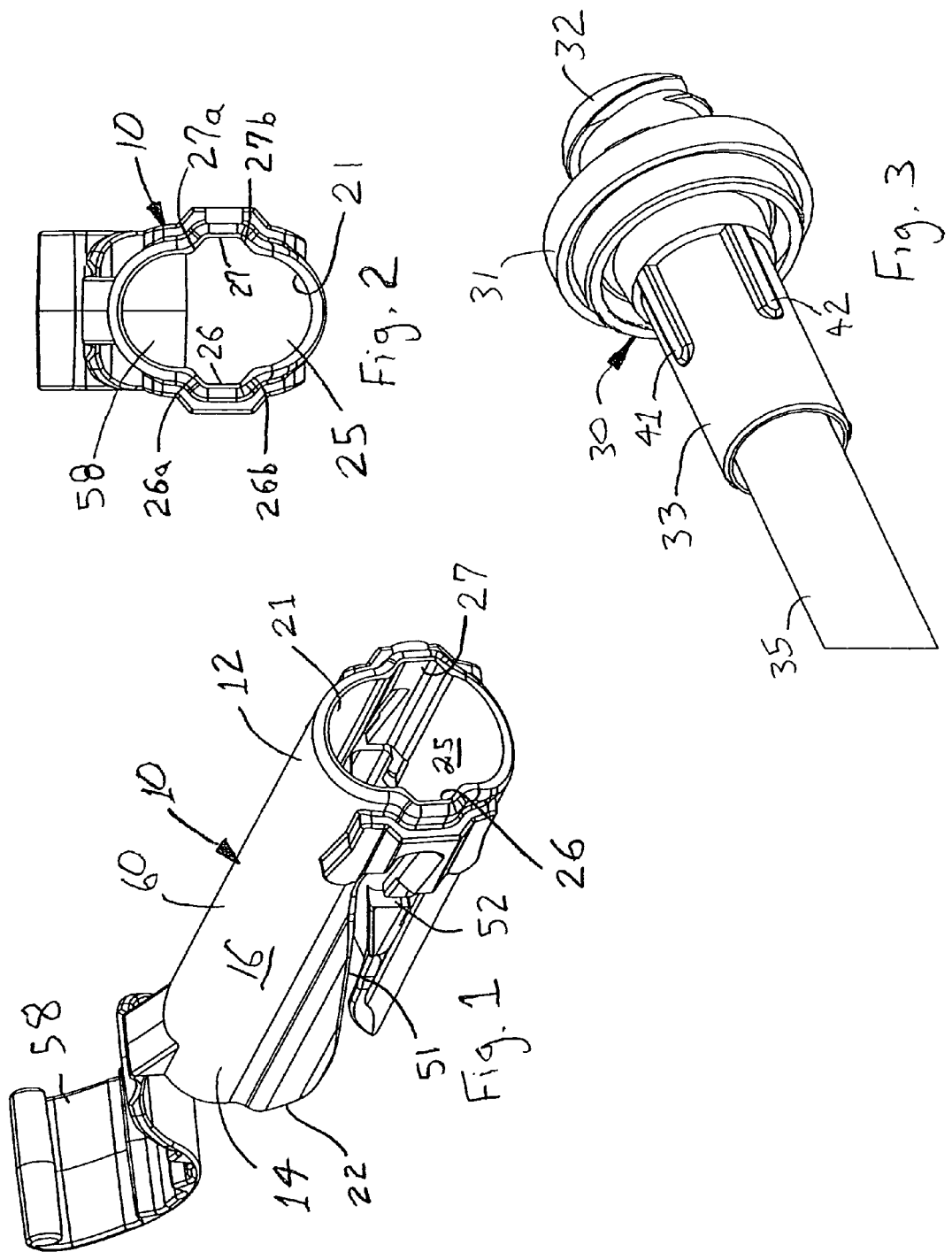

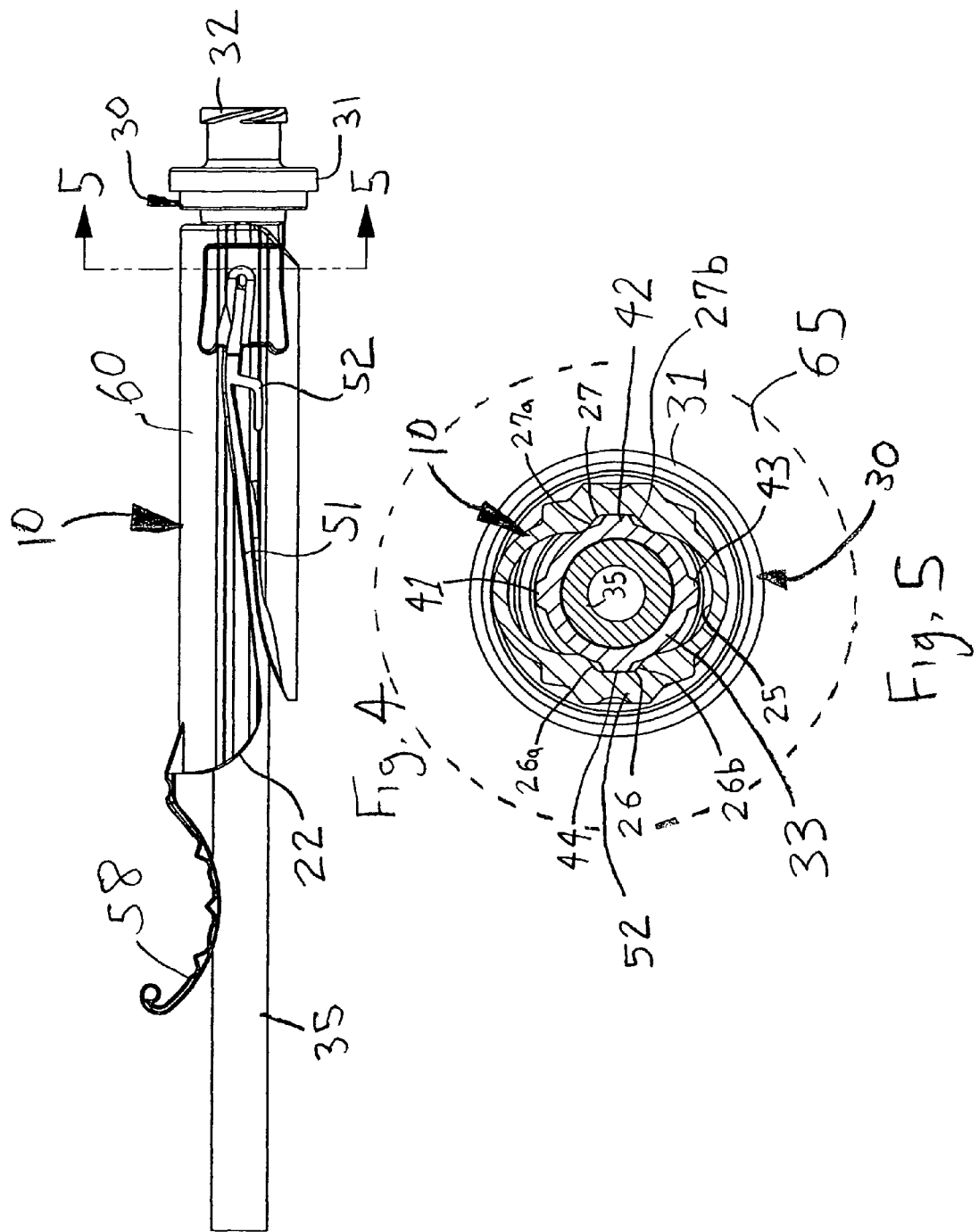

MEDICAL TUBING SET SHEATH

The present invention pertains to a sheath which may be attached to a connector of a medical tubing assembly. The sheath may also act as a torquing member to help connect the tubing assembly to a peripheral tubing assembly.

BACKGROUND

Needle protection devices are well-known that are assembled to a medical tubing assembly for protecting a needle after it is removed from a patient. For example, U.S. Pat. No. 5,772,638 depicts a protector for a needle including a sheath having slotted side walls to receive a winged needle. The sheath slides along the tubing to cover the needle, so that the sharp tip of the needle is recessed inside the sheath and cannot cause accidental injury. The sheath is locked to the needle so that it cannot be easily removed from its protecting position over the needle. While such needle guards work well to protect the needle in the protecting position; prior to locking the sheath in place over the needle, the sheath slides freely along the tubing, which may cause problems with the operation of the tubing set. For example, an arteriovenous fistula needle set for hemodialysis may have a tubing length of approximately six to twelve inches. When the sheath can slide freely between the needle and a connector at the opposite end, it is difficult to quickly locate the sheath, in order to place it over the needle. As well, if the sheath is sliding freely on the tubing, for example, during shipping, the sheath may prematurely slide to its protecting position covering the needle, so that when the tubing set is removed from its packaging the needle is not exposed for quick insertion into a patient's arm. Thus, it is desirable to retain the sheath in a predetermined, displaced position along the tubing, so that the sheath may have a spaced resting place, prior to placement of the sheath in its protecting position over the needle.

Such tubing sets commonly have a connector at an end for connection of the tubing set to a peripheral or secondary tubing set. The connector may have a threaded coupling or a luer type coupling for connection to a corresponding coupling of a secondary tubing set. Commonly, the connector includes a collar for receiving the tubing therein. The collar is generally grabbed by a user's fingers in order to attach the connector to the secondary tubing set. Generally, the collar has an outer diameter of about 4 mm, and due to its small size is difficult to grab, and to impart sufficient pressure by the user's fingers in order to torque the connector properly. For example, because the collar of the connector is difficult to grip properly, in some circumstances, the connector may not be fastened tightly enough to the secondary tubing set and can disconnect—causing blood or other fluids to spill and escape the tubing sets.

In other circumstances, the connector becomes attached to a secondary tubing set too tightly, and is later difficult to remove. For example, during usage of the tubing sets blood may flow through the tubing sets, and warm up the connector. Such heat may cause expansion of the plastic components, that may result in tightening of the coupling and make it difficult later to remove or disconnect the couplers/connectors. As the collar of the connector has such a small diameter, it may be difficult to adequately grip the coupling in order to generate sufficient torque in order to remove the connector from the secondary tubing. Thus, there is desired a means for more securely and more easily gripping and attaching a connector of a first tubing set to a second tubing set. It is also desirable to provide a ratcheting means to avoid over-torquing the connector of a tubing set.

SUMMARY

In order to overcome the disadvantages of previous devices, the present invention provides for a needle protector sheath slidably mounted to a medical tubing set between a needle and a tubing connector, the sheath comprising a needle receiving portion, and a retention portion for attaching the sheath to the connector, so that the sheath is prevented or restrained from sliding along the tubing. In an embodiment, the sheath may include a main body including a first end forming the retention portion and a second end opposite the first end for receiving the needle. In an embodiment, the connector may include a collar, and the retention portion may form a bore having a corresponding shape to the collar, the bore providing a friction fit to the collar. In an embodiment, the connector may include a longitudinal rib and the retention portion may include a groove for receiving the longitudinal rib, and a friction fit provided between the longitudinal rib and the groove, in order to retain the sheath to the connector.

In an embodiment, the connector may include a cylindrical collar having an outer diameter, and the retention portion may have a cylindrical bore having an inner diameter which is the same or slightly larger than the outer diameter of the collar, for engaging the collar to attach the sheath to the connector. In an embodiment, the connector may be cylindrical, and may include radially spaced engagement members, and the retention portion may include grooves for engaging the engagement members.

In an embodiment, the engagement members may be disposed at 90 degree intervals around a circumference of the connector, and the retention portion may include at least two grooves for receiving at least two of the engagement members when the retention portion engages the connector. In a particular embodiment, the groove may be proportionally shaped with respect to the engagement member so that, upon application of a predetermined torque, the engagement member will be released from the groove in order to provide a ratcheting function of the retention portion. The retention portion may allow for proper connection of the connector to a peripheral tubing set due to the ratcheting function of the retention portion.

The sheath may form a handle along an exterior body of the sheath to allow for a user's finger and/or thumb to easily grip the sheath. In some embodiments, the needle receiving portion of the sheath may include a slot for receiving wings protruding from a needle of a fistula set, so that upon removal of the retention portion from the connector, the sheath may slidingly cover the needle.

In an embodiment, the retention portion may include a ratcheting groove for engaging an engagement member of the connector so that torque may be applied by the sheath through the connector and allow for ratcheting upon application of a predetermined amount of torque. In some embodiments, the torque applied to cause ratcheting may equal approximately a value in a range of 0.5 to 0.8 inch pounds. The connector may be a luer connector, and it may include a front end having a luer portion and an opposite collar for engaging the retention portion of the sheath. In another embodiment, the connector may be mounted along the tubing set, spaced from a second connector which provides for attachment of the tubing set to a peripheral tubing set.

In some embodiments, the invention provides for a medical tubing connector and sheath assembly comprising a connector attached to an end of medical tubing, the connector having a collar for receiving the end of the medical tubing, and a sheath slidably mounted on the tubing, the sheath including a retention portion for attaching the collar to the connector. In some embodiments, a ratcheting portion is provided for allowing a predetermined torque to be applied to the connector, to allow for proper connection of the connector to a peripheral tubing set. If desired, the sheath may form a handle along an exterior body of the sheath to allow for a user's finger and/or thumb to easily grip the sheath. In some embodiments, the handle may have an outer diameter greater than 4 mm. In some embodiments, the sheath may include a needle receiving portion in order to cover a needle of a fistula set.

In another embodiment of the invention, a method of attaching a medical tubing connector to a peripheral tubing set is provided that comprises the steps off providing a tubing set including a connector having a collar for receiving an end of the tubing and a sheath having a retention portion for attaching to the collar, mating the connector to a peripheral tubing set by abutting a mating end of the connector to the peripheral tubing set, sliding the retention portion over the collar, rotating the retention portion to apply torque to the connector in order to attach the connector to the peripheral tubing set, and optionally ratcheting the retention portion of the collar upon application of torque by the retention portion greater than needed to mate the connector to the peripheral tubing set.

In an embodiment, the method may further comprise the step of sliding the sheath retention portion off of the collar, and advancing it to cover a needle extending from the medical tubing. In an embodiment, the method may further comprise the step of imparting torque to the retention portion in order to rotate the connector for rotational connection to a peripheral tubing set. In an embodiment the method may comprise the step of sliding the retention portion over the collar so that a groove of the retention portion engages a rib protruding from the side of the collar and frictionally engaging the retention portion. In an embodiment, the method may comprise the step of forming a ratcheting portion of a flexible polymer material so that upon applying torque to the retention portion against the rib, the retention portion may flex in order to release the rib from the groove.

In an embodiment, the method may further comprise the step of orienting the retention portion on the connector to provide a flat profile for the assembly to allow for placement in a narrow package. In an embodiment, the method may further comprise the step of tuning the ratcheting function during manufacture of the retention portion to provide different levels of torque for various connector types. In an embodiment, the method may further comprise the step of grasping the retention portion firmly by a user's hand so that the proper amount of torque may be applied to mate the connector to a peripheral tubing set.

In an embodiment, the medical tubing connector may comprise retention means for reversibly retaining other tube set components other than a needle protector sheath. For example, a tubing clamp typically is found on the tubing connected to a medical tubing connector. Such clamp may be reversibly positioned on said connector retention means out of the way of the procedure, until needed.

BRIEF DESCRIPTION OF THE DRAWINGS

There is shown in the drawings a preferred embodiment of the present invention, wherein like numerals in the various figures pertain to like elements, and wherein:

FIG. 1 is a perspective view of a sheath of the present invention;

FIG. 2 is an end view of the sheath of FIG. 1;

FIG. 3 is a perspective view of a connector attached to an end of a tubing set;

FIG. 4 is a side elevation view of the sheath of FIG. 1 attached to the tubing set of FIG. 3;

FIG. 5 is a sectional view of FIG. 4 taken at line 5-5; and

DETAILED DESCRIPTION OF SPECIFIC EMBODIMENTS

Figure 6:
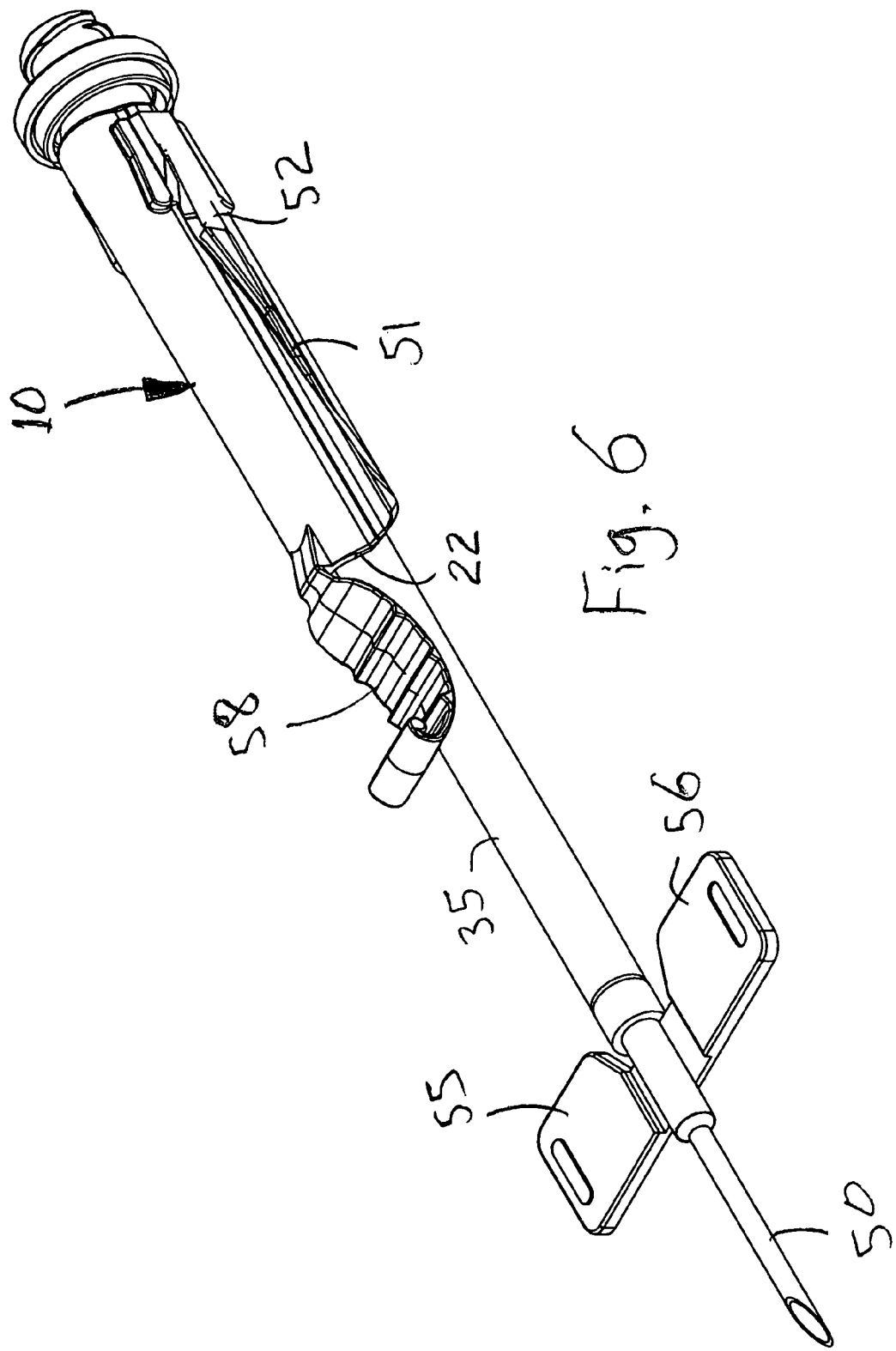
FIG. 6 is a perspective view of a sheath of the present invention mounted to a fistula tubing set.

An embodiment of the present invention is described with respect to FIGS. 1-6. A sheath 10 includes a retention portion 12. Sheath 10 may provide for needle protection in a known manner and includes a needle receiving portion 14. In another embodiment, the sheath 10 need not have a needle receiving portion. Sheath 10 may be formed of a polymer material such as a translucent PP forming a generally cylindrically shaped main body 16 having a first end 21 and second end 22 for receiving a needle.

FIG. 2 is an end view of the sheath 10 and shows that the sheath 10 is generally oval in cross-section. A bore 25 extends generally between the first end 21 and the second end 22 of the sheath 10. The bore 25 may be generally oval shaped along the entire longitudinal axis of the sheath 10. As shown in FIG. 2, the oval shape of the body 16 at the first end 21 is interrupted by a pair of internal grooves 26, 27 formed in each side of the body 16 of the sheath 10. In an embodiment, each groove 26, 27 forms the retention portion 12 and a ratcheting means, and includes shoulders 26a, b and 27a, b.

Each groove 26, 27 and shoulders 26a, b, 27a, b provide for a retention mechanism in order to attach the sheath 10 to an engagement member formed on a tubing set. For example as shown in FIG. 3, a connector or coupler 30 includes a flange 31 and a rotational engagement mechanism 32 such as a threaded coupling or a luer connector. Opposite the coupling 32 is a collar 33. Tubing 35 of a medical tubing set is terminated within the collar 33 of the connector 30. The collar 33 is cylindrical and includes an outer diameter that is corresponding in size to the bore 25 of the sheath 10. In the embodiment shown, the collar 33 includes engagement members 41, 42 that are longitudinal ribs protruding from the collar 33 (FIG. 3). In an embodiment four ribs 41-44 (FIG. 5) are provided, which are radially disposed at 90° positions around the circumference of the collar 33. The height of each rib 41, 42 is approximately equal to the depth of each corresponding groove 26, 27 to which the ribs 41, 42 are mated when the sheath 10 is slid over the collar 33 (FIGS. 4-6). Thus, upon positioning of the grooves 26, 27 over the corresponding ribs, a frictional engagement between the ribs and the grooves 26, 27 is provided in order to frictionally retain the sheath 10 on the collar 33 of the connector 30.

For example, as shown in FIG. 5, the ribs 42, 44 are mated with the grooves 26, 27 and the sides of the ribs 42, 44 frictionally engage the inner walls of the grooves 26, 27, in order to maintain the sheath 10 on the collar 33 of the connector 30. Thus, it can be understood that the sheath 10 can be retained in its preliminary position attached to the connector 30, prior to the time in which the sheath may be used as a needle protector; whereby the sheath 10 is slid along the tubing 35 toward the needle 50 (FIG. 6) in order to protect the needle after it is withdrawn from a patient's skin.

The sheath 10 may also include slots 51 and catch projections 52 for receiving the wings 55, 56 protruding from the needle assembly; so that when the sheath 10 is slid over the needle 50 of the fistula set, the wings 55, 56 are locked in position so that the sheath 10 cannot be easily slid backward down the tubing 35 to expose the needle 50 after it has been used. A detailed description of the needle guard feature of the sheath 10 is described in U.S. Pat. No. 5,772,638 which is incorporated herein by reference. The sheath 10 also includes a finger shield 58.

Body 16 comprises a handle 60 which extends along the outer diameter of the sheath 10 and provides a gripping surface for a user's finger and/or thumb. In an embodiment, the outer diameter of the sheath is greater than 4.0 mm, and may include a smooth or textured surface in order to allow for easy gripping of the handle 60 by a user's fingers or thumb. The handle 60 allows for the user to grasp the sheath 10 and use the sheath and the retention portion 12 as a tool in order to help attach the tubing set 35 to a secondary or peripheral tubing set (not shown).

For example, when sheath 10 is provided in its displaced position, as shown in FIG. 4, it engages the collar or sleeve 33 of connector 30. In order to attach the connector 30 to an adjacent coupling, the threaded end 32 is abutted against the corresponding coupler of the peripheral tubing set. A user grasping the sheath handle 60, for example, between a finger and a thumb, may rotate the handle 60, which in turn transfers a rotational force to the connector 30 via the grooves 26, 27 engaging the engagement members 41-44, and causes the coupling end 32 to rotate. Due to the handle 60 having gripping surface for the user's finger and thumb and also having a larger diameter than the underlying collar 33 of the connector 30, a user may more easily provide the proper amount of torque to be applied to the connector 30, in order to easily and fully couple it to a peripheral tubing set. Thus, it is more likely that the tubing set 35 will be properly attached to a peripheral tubing set, and the connector 30 will be properly attached with enough torque to a corresponding coupler, so that the connection will not come apart easily, or be overtightened so that removal of the tubing set at a later time is difficult.

Thus, it is understood that the present invention provides for a retention location for the sheath 10 during shipment that is remote from an attached needle, so that the sheath 10 will not be dislocated during shipment, and upon removal of the tubing assembly from the packaging, the needle will not be covered by the sheath 10, and the needle can be quickly inserted in a patient's arm. The handle 60 of the sheath helps to ensure that if the connector 30 seizes, additional torque can be applied by firmly grasping the handle 60 and squeezing the sheath 10 in order to impart additional torque to remove the seized connector and allow it to be removed from a corresponding coupling. The ability to disconnect the connector 30 will, for example, alleviate the difficulty of having to remove a catheter from a patient's arm when the connector has seized and cannot be disconnected.

In order to further ensure that the connector 30 is properly rotated, the sheath 10 may include a ratcheting mechanism. In an embodiment, the geometry and polymer materials of the ribs 41-44 and the grooves 26, 27 provide a ratcheting mechanism. The depth of the grooves 26, 27 are formed to a predetermined shape so that upon application of too much torque to the sheath 10; the ribs 41, 44 will engage the walls of the sheath 10 and cause the body 16 to flex outward and allow the ribs 41-44 to exit the grooves 26, 27 (so that additional torqueing does not occur by the sheath 10). For example, upon application of too much torque, the rib 42 will abut against the shoulder 27a of groove 27 and will cause the outer wall of the sheath 10 to flex outwardly so that the sheath 10 may rotate while the connector 30 maintains its position. In this way, due to the ratcheting feature, additional excess torque will not be transferred by the sheath 10 through the connector 30 to the corresponding coupling of a peripheral tubing set.

In an embodiment, a torque measurement ($\tau=r \times F$) of 0.5 to 0.8 inch pounds can be provided for in order to attach a standard luer connector 30 to a corresponding peripheral tubing set. A rib 41-44 having a height of approximately 0.5 mm and a width of 1.2 mm and a corresponding groove 26, 27 having a depth of approximately 0.8 mm and a width of 2.0 mm formed of a plastic having a 60 R to 70M scale will provide for a sufficient ratcheting mechanism that may occur at about 0.8 inch pounds. Other geometries and hardnesses can also provide for a retention/ratcheting duel functionality of the retention portion 12 of the sheath.

It is to be understood that the retention portion 12 of the sheath 10 may be tuned during manufacture of the sheath 10 in order to provide for varying torque measurements, by changing the geometry of the retention portion such as the depth and shape of the grooves 26, 27. Also different polymers may be used to affect (tune) the flexing or resilience of the sheath 10. It is also to be understood that other types of retention mechanisms other than grooves and ribs may be provided. For example, couplings, fasteners, detentes, hooks, joints, keys, latches, lugs, pins, journals, pivots, fingers, blades, belts and plugs may be provided by the retention portion 12 or the collar 33, in order to retain the sheath 10 to the connector 30 and also to provide for a ratcheting mechanism. As well, it is to be understood that the engagement members 41-44 may be provided on a structure other than the connector formed at the terminal end of the tubing set 35. For example, an intermediate connector or coupler may be provided along the tubing set, so that the sheath 10 may be retained more closely to the needle 50, when the sheath 10 is in its displaced, preliminary position (prior to removal of the needle from a patient's skin).

The present invention also provides for a method of attaching a medical tubing connector 30 to a peripheral tubing set 65 (FIG. 5). The method includes mating the connector 30 to the peripheral tubing set by abutting a mating end 32 of the connector 30 to the peripheral tubing set (and before or after that step), the retention portion 12 of the sheath 10 is then slid over the collar 33 in order to engage a engagement member 41 of the collar 33. The retention portion 12 is then rotated to impart torque to the connector 30 in order to attach the connector 30 to the peripheral tubing set. The retention portion 12 may be ratcheted on the collar 33 upon application of torque that is greater than is needed to mate the connector 30 to the peripheral tubing set. The retention portion 12 of the sheath 10 provides ratcheting by the engagement of grooves 26, 27 on the engagement members 41, 44. The flexibility of the retention portion 12 allows for the ratcheting mechanism to occur upon application of excess torque.

The predetermined orienting of the sheath 10 during shipping is also a benefit of the present invention. Orienting the grooves 26 with respect to the finger shield 58 and wings 55, 56 in a predetermined orientation with respect to the connector 30, allows the finger shield 58 or wings 55, 56 to provide for the lowest possible profile, so that the assembly may be placed in a narrow/flat package where the shield 58 is oriented to protrude in the same plane as the wings 55, 56. It is also to be understood that the handle 60 allows the sheath 10 to be easily gripped, in order to easily slide the sheath 10 off of the connector 30, down the tubing 35 and around a needle 50 (after the needle is removed from a patient's skin).

The above description is offered for illustrative purposes only and is not intended to limit the scope of the invention which is defined in accordance with the claims below.

The invention claimed is:

1. A medical tubing connector and sheath assembly comprising:
a connector attached to an end of medical tubing, the connector having a collar and the connector receiving the end of the medical tubing;
a sheath slidably mounted on the tubing, the sheath including a retention portion for attaching to the collar of the connector, wherein the sheath includes a needle receiving portion having slots for receiving wings protruding from a needle of a fistula set so that upon removal of the retention portion from the connector, the sheath may slidingly cover the needle; and
a ratcheting portion for allowing for a predetermined maximum torque to be applied to the connector to allow for proper connection of the connector to a peripheral tubing set.

2. The assembly of claim 1 wherein the sheath forms a handle along an exterior body of the sheath to allow for a user's finger and/or thumb to easily grip the sheath.

3. The assembly of claim 2 wherein the handle has an outer diameter greater than 4.0 mm.

4. The assembly of claim 1 wherein the sheath includes a needle receiving portion in order to cover a needle attached to the medical tubing.

5. The assembly of claim 1 wherein the sheath includes a main body including a first end forming the retention portion and a second end opposite the first end for receiving a needle.

6. The assembly of claim 1 wherein the retention portion forms a bore having a corresponding shape to the collar, the bore providing a friction fit to the collar, and wherein torque imparted to the sheath can be transferred to the connector.

7. A medical tubing connector and sheath assembly comprising:
a connector attached to an end of medical tubing, the connector having a collar and the connector receiving the end of the medical tubing;
a sheath slidably mounted on the tubing, the sheath including a retention portion for attaching to the collar of the connector, wherein the sheath includes a needle receiving portion having slots for receiving wings protruding from a needle of a fistula set so that upon removal of the retention portion from the connector, the sheath may slidingly cover the needle;
wherein the connector includes at least one longitudinal rib, and the retention portion includes at least one groove for receiving the longitudinal rib, with a friction fit being provided between the longitudinal rib and the groove in order to retain the sheath to the connector.

8. The assembly of claim 1 wherein the collar is cylindrical having an outer diameter and the retention portion has a cylindrical bore, said bore having an inner diameter and the inner diameter being equal to or slightly larger than the outer diameter of the collar and engaging the collar in order to attach the sheath to the connector.

9. A medical tubing connector and sheath assembly comprising:
a connector attached to an end of medical tubing, the connector having a collar and the connector receiving the end of the medical tubing;
a sheath slidably mounted on the tubing, the sheath including a retention portion for attaching to the collar of the connector, wherein the sheath includes a needle receiving portion having slots for receiving wings protruding from a needle of a fistula set so that upon removal of the retention portion from the connector, the sheath may slidingly cover the needle,
wherein the connector is cylindrical and includes radially spaced engagement members, and the retention portion includes grooves for engaging the engagement members.

10. The assembly of claim 9 wherein the engagement members are disposed at 90 degree intervals around a circumference of the connector, and the retention portion includes at least two grooves for receiving at least two of the engagement members when the retention portion engages the connector.

11. The assembly of claim 9 wherein the grooves are proportionally shaped with respect to the engagement members so that, upon application of a predetermined torque, the engagement members will be released from the grooves in order to provide a ratcheting function of the retention portion.

12. The assembly of claim 11 wherein the retention portion allows for proper torque connection of the connector to a peripheral tubing set due to the ratcheting function of the retention portion.

13. A medical tubing connector and sheath assembly comprising:
a connector attached to an end of medical tubing, the connector having a collar and the connector receiving the end of the medical tubing;
a sheath slidably mounted on the tubing, the sheath including a retention portion for attaching to the collar of the connector, wherein the sheath includes a needle receiving portion having slots for receiving wings protruding from a needle of a fistula set so that upon removal of the retention portion from the connector, the sheath may slidingly cover the needle,
wherein the retention portion includes a ratcheting groove for engaging an engagement member of the connector so that a rotational force may be applied by the sheath through the connector, and to allow for said ratcheting upon application of a predetermined amount of torque.

14. A medical tubing connector and sheath assembly comprising:
a connector attached to an end of medical tubing, the connector having a tubing collar and receiving the end of the medical tubing;
a sheath slidably mounted on the tubing, the sheath including a retention portion for attaching to the collar of the connector, including a handle along an exterior thereof for a user's finger and/or thumb to easily grip the sheath, the handle including a portion contoured for a finger shield; and
a ratcheting portion for allowing for a predetermined maximum torque to be applied to the connector to allow for proper connection of the connector to a peripheral tubing set.

15. A medical tubing connector and sheath assembly comprising:
a connector attached to an end of medical tubing, the connector having a tubing collar and receiving the end of the medical tubing;
a sheath slidably mounted on the tubing, the sheath including a retention portion for attaching to the collar of the connector, including a handle along an exterior thereof for a user's finger and/or thumb to easily grip the sheath, the handle including a portion contoured for a finger shield, wherein the connector includes at least one longitudinal rib, and the retention portion includes at least one groove for receiving the longitudinal rib, with a friction fit being provided between the longitudinal rib and the groove in order to retain the sheath to the connector.

16. A medical tubing connector and sheath assembly comprising:
- a connector attached to an end of medical tubing, the connector having a tubing collar and receiving the end of the medical tubing;
- a sheath slidably mounted on the tubing, the sheath including a retention portion for attaching to the collar of the connector, including a handle along an exterior thereof for a user's finger and/or thumb to easily grip the sheath, the handle including a portion contoured for a finger shield, wherein the connector is cylindrical and includes radially spaced engagement members, and the retention portion includes grooves for engaging the engagement members.

17. The assembly of claim 16 wherein the engagement members are disposed at 90 degree intervals around a circumference of the connector, and the retention portion includes at least two grooves for receiving at least two of the engagement members when the retention portion engages the connector.

18. The assembly of claim 16 wherein the grooves are proportionally shaped with respect to the engagement members so that, upon application of a predetermined torque, the engagement members will be released from the grooves in order to provide a ratcheting function of the retention portion.

19. The assembly of claim 18 wherein the retention portion allows for proper torque connection of the connector to a peripheral tubing set due to the ratcheting function of the retention portion.

20. A medical tubing connector and sheath assembly comprising:
- a connector attached to an end of medical tubing, the connector having a tubing collar and receiving the end of the medical tubing;
- a sheath slidably mounted on the tubing, the sheath including a retention portion for attaching to the collar of the connector, including a handle along an exterior thereof for a user's finger and/or thumb to easily grip the sheath, the handle including a portion contoured for a finger shield, wherein the retention portion includes a ratcheting groove for engaging an engagement member of the connector so that a rotational force may be applied by the sheath through the connector, and to allow for said ratcheting upon application of a predetermined amount of torque.

21. A medical tubing connector and sheath assembly comprising:
- a connector attached to an end of medical tubing, the connector having a collar and receiving the end of the medical tubing;
- a sheath slidably mounted on the tubing and having a retention portion and a handle portion; and
- a ratcheting portion for attaching to the collar and the sheath retention portion, wherein the ratcheting portion allows for a predetermined maximum torque to be applied to the connector for proper connection of the connector to a peripheral tubing set.

22. The assembly of claim 21 wherein the handle portion may be compressed to increase the maximum torque allowed by the ratcheting portion to be applied to the connector.

23. The assembly of claim 21 wherein the sheath includes a needle receiving portion in order to cover a needle attached to the medical tubing.

24. The assembly of claim 21 wherein the ratcheting portion includes a bore formed on the sheath retention portion, the bore having a corresponding shape to the collar, the bore providing a friction fit to the collar, and wherein torque imparted to the sheath can be transferred to the connector.

25. The assembly of claim 21 wherein the connector includes at least one longitudinal rib, and the retention portion includes at least one groove for receiving the longitudinal rib, with a friction fit being provided between the longitudinal rib and the groove in order to retain the sheath to the connector.

26. The assembly of claim 21 wherein the collar is cylindrical having an outer diameter and the retention portion has a cylindrical bore, said bore having an inner diameter and the inner diameter being equal to or slightly larger than the outer diameter of the collar and engaging the collar in order to attach the sheath to the connector.

27. The assembly of claim 21 wherein the connector is cylindrical and includes radially spaced engagement members, and the retention portion includes grooves for engaging the engagement members.

28. The assembly of claim 27 wherein the engagement members are disposed at 90 degree intervals around a circumference of the connector, and the retention portion includes at least two grooves for receiving at least two of the engagement members when the retention portion engages the connector.

29. The assembly of claim 27 wherein the grooves are proportionally shaped with respect to the engagement members so that, upon application of a predetermined torque, the engagement members will be released from the grooves in order to provide a ratcheting function of the retention portion.

30. The assembly of claim 29 wherein the retention portion allows for proper torque connection of the connector to a peripheral tubing set due to the ratcheting function of the retention portion.

31. The assembly of claim 21 wherein the sheath includes a needle receiving portion having slots for receiving wings protruding from a needle of a fistula set, so that upon removal of the retention portion from the connector, the sheath may slidingly cover the needle.

32. The assembly of claim 21 wherein the retention portion includes a ratcheting groove for engaging an engagement member of the connector so that a rotational force may be applied by the sheath through the connector, and to allow for said ratcheting upon application of a predetermined amount of torque.

* * * * *